United States Patent [19]

Basset et al.

[11] Patent Number: 4,654,462
[45] Date of Patent: Mar. 31, 1987

[54] METATHESIS OF OLEFINS WITH A CATALYST BASED UPON A TUNGSTEN COMPLEX

[75] Inventors: Jean M. Basset; Michel Leconte, both of Villeurbanne; Jean Ollivier, Arudy; Francoise Quignard, Lyons, all of France

[73] Assignee: Societe Nationale Elf Aquitaine, France

[21] Appl. No.: 826,565

[22] Filed: Feb. 6, 1986

[30] Foreign Application Priority Data

Feb. 12, 1985 [FR] France .................... 85 01930

[51] Int. Cl.$^4$ .......................... C07C 6/00; B01J 31/34
[52] U.S. Cl. .................... 585/646; 502/102; 502/117; 585/643
[58] Field of Search .............. 585/643, 644, 645, 647, 585/646; 502/102, 117, 167, 168, 171

[56] References Cited

U.S. PATENT DOCUMENTS

| | | | |
|---|---|---|---|
| 4,247,417 | 1/1981 | Banasiak | 585/645 |
| 4,248,738 | 2/1981 | Banasiak | 585/645 |
| 4,262,156 | 4/1981 | Banasiak | 585/645 |
| 4,269,780 | 5/1981 | Banasiak | 585/645 |
| 4,291,187 | 9/1981 | Banasiak | 585/645 |
| 4,550,216 | 10/1985 | Basset et al. | 585/645 |

OTHER PUBLICATIONS

M. Leconte, Y. Ben Taarit, J. L. Bilhou and J. M. Basset, "Journal of Molecular Catalysis", 8 (1980) pp. 263–268.

J. M. Basset, G. Coudurier, R. Mutin and H. Praliaud, "Journal of Catalysis", 34 (1974) pp. 152–155.
R. H. Grubbs, "Comprehensive Organometallic Chemistry", 8(54) (1982) pp. 499–551.
J. L. Bilhou, J. M. Basset, R. Mutin and W. F. Graydon, "Journal of American Chemical Society", 99 (1977) pp. 4083–4090.
T. J. Katz and W. H. Hersh, "Tetrahedron Letter", No. 6, (1977) pp. 585–588.

Primary Examiner—Asok Pal
Attorney, Agent, or Firm—Ostrolenk, Faber, Gerb & Soffen

[57] ABSTRACT

Improved process of metathesis of olefins by contact of one or more olefins with a catalyst comprising a tungsten complex with two phenoxy groups, carrying substituents and four other ligands, the complex carrying as coordination groups a halogen atom, an alkyl radical and a carbene. The catalyst preferably is of the formula

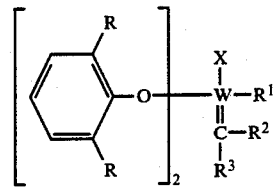

where X is halogen, R is hydrocarbon or an electronegative group or atom, $R^1$ is alkyl and $R^2$ and $R^3$ are individually hydrogen or alkyl groups.

17 Claims, No Drawings

METATHESIS OF OLEFINS WITH A CATALYST BASED UPON A TUNGSTEN COMPLEX

The invention relates to an improvement in the metathesis of various olefins by the use of an improved catalyst. It includes this particular catalyst, comprising an organic tungsten complex, as a new industrial product.

Metathesis, that is rearrangement, of olefins has been the subject of numerous studies in recent times, because of the practical interest which it has. A substantial advance in the choice of more interesting catalysts is described in French Patent Application Nos. 8309876 and 8409001. The first of these publications relates to catalysts of the type

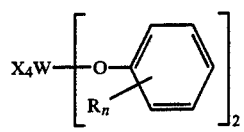
(1)

where X is a halogen, R is a hydrocarbon group, an electronegative group or atom and n is an integral number from 1 to 5. Such catalysts associated with Al or Sn compounds have allowed the rearrangement of various olefins more rapidly than can be done with prior art catalysts. According to the second of the patents mentioned, the activity of the new catalyst is increased further by the addition of Pb compounds in place of Sn compounds.

The present invention relates to an improvement in comparison with the prior art, including the disclosures of the publications mentioned above. In effect, the use of a catalyst according to the invention allows a metathesis which is as rapid or is more rapid, without a co-catalyst, and moreover both for olefins carrying functional groups as well as for those which do not carry them.

Moreover, the addition of a Lewis acid co-catalyst, for example organo metallic compounds based on Al, Sn, Pb, Mg or Ti such as are described and known in the art of olefin metathesis and particularly in Patent Applications 8309876 and 8409001, leads to even more active catalyst systems.

Another advantage of the invention over the known art is that it makes possible the use of catalysts having both a good activity and a stereo-selectivity. An excellent stereo-selectivity can thus be obtained even at rates which approach maximum conversions, corresponding to equilibrium of the metathesis reaction. If reference is made to the technical literature, particularly R H GRUBBS, "Comprehensive Organometallic Chemistry", 8(54) (1982) p. 499-551, J M BASSET, G. COUDURIER, R. MUTIN and H. PRALIAUD, "Journal of Catalysis", 34 (1974) p.152-155, J L BILHOU, J M BASSET, R MUTIN and W F GRAYDON, "Journal of American Chemical Society", 99 (1977) p.4083-4090, M LECONTE, Y BEN TAARIT, J L BILHOU and J M BASSET, "Journal of Molecular Catalysis", 8 (1980) p.263-268, very few metathesis catalysts exhibit stereo-selectivity even at low conversions; on the other hand, it also seems from this literature that with most standard catalyst systems when the conversion of the metathesis reaction increases it produces in parallel a cis-trans isomerization; for the products of the reaction, this involves a loss in stereo-selectivity which with the advance of the reaction rapidly approaches the values given by thermodynamic equilibrium.

A case of a stereo-selective catalyst has been cited by T J KATZ and W H HERSH, "Tetrahedron Letters", n°6, (1977) p.585-588. However, as this article indicates, this catalyst appears on the one hand to have very little activity and on the other to be stereo-selective uniquely in the metathesis of cis-2-pentene, while it is not in the case of the metathesis of trans-2-pentene. The catalyst of the present invention provides an important advance since it is more active and can effect in a stereo-selective manner both the metathesis of a cis-olefin and that of a trans-olefin.

For all these reasons, in particular the fact of their stereo-selectivity, the catalysts of the invention are very interesting for the synthesis of insect pheromones. Several of these compounds can be obtained by the metathesis of olefins carrying functional groups and they are often biologically active only in a pre-determined stereo-chemical form (cis or trans).

The improved catalyst according to the invention constituted by a di-phenoxy tungsten complex is characterised in that its other coordination groups or ligands comprise at least one halogen and hydrocarbon groups, one of which is a carbene.

In a general manner, this catalyst can be represented by the formula

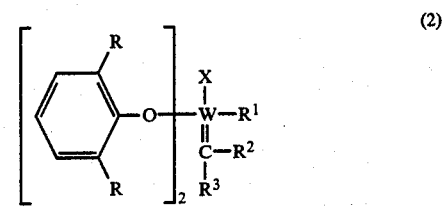
(2)

where X is a halogen, R is a hydrocarbon group or an electronegative group or atom, $R^1$ is an alkyl group, preferably $C_1$ to $C_8$ and straight or branched, and $R^2$ and $R^3$ are hydrogen atoms or straight or branched $C_1$ to $C_8$ alkyl groups; $R^1$, $R^2$ and $R^3$ can be the same or different.

Preferred R groups are $C_1$ to $C_6$ alkyls, phenyls and Cl, Br or F atoms.

The groups $R^1$, $R^2$ and $R^3$, the same or different, comprise for example the following straight or branched groups:

| | |
|---|---|
| $-CH_3$, $-(CH_2)_n-CH_3$ | (n integral number ranging from 1 to 7) |
| $-(CH_2)_{n1}-CH\begin{smallmatrix}(CH_2)_{n2}-CH_3\\(CH_2)_{n3}-CH_3\end{smallmatrix}$ | ($n_1$, $n_2$, $n_3$ integral numbers which are the same or different and range from 0 to 5 with $0 \leq n_1 + n_2 + n_3 \leq 5$) |
| $-(CH_2)_{n1}-C\begin{smallmatrix}(CH_2)_{n2}-CH_3\\(CH_2)_{n3}-CH_3\\(CH_2)_{n4}-CH_3\end{smallmatrix}$ | ($n_1$, $n_2$, $n_3$, $n_4$ integral numbers which are the same or different and range from 0 to 4 with $0 \leq n_1 + n_2 + n_3 + n_4 \leq 4$) |

Moreover, $R^2$ or $R^3$ or both can be hydrogen atoms. Finally, $R^2$ and $R^3$ can be part of the same hydrocarbon chain, for example:

in which $4 \leq n \leq 10$.

In a preferred form of the invention, the groups $R^1$, $R^2$ and $R^3$ are such that the group $R^1$ can be written in the form

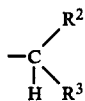

By way of example, in one particularly preferred form, $R^1$ is a neo-pentyl group

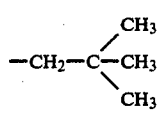

$R^2$ is a tertio-butyl group

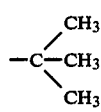

and $R^3$ is a hydrogen atom.

Tungsten complexes having a carbene ligand, usable in the metathesis reaction of olefins, have been described in French Pat. No. 8206631; however these catalysts must have two different metals in their formula and a Lewis acid compound. They are thus notably different from the catalysts of the present invention, because the latter only require a single metal and do not necessarily include a Lewis acid compound.

The catalysts of the invention can be obtained by reacting a phenoxy tungsten complex of formula (1) with an organo-magnesium compound of the general formula $Mg(CHR'R'')_2$ (dioxan) where $R'$ and $R''$ are hydrogen atoms or alkyl hydrocarbon groups. In a particular preferred embodiment, $R'$ is a hydrogen atom and $R''$ is a tertio-butyl group: $C(CH_3)_3$. The organo-magnesium/phenoxy tungsten molar ratio used in the reaction is preferably 1.5. The reaction is carried out in a solvent, generally ether, which can be an acyclic or cyclic ether. Preferably this ether is for instance dimethyl ether, diethyl ether, diisopropyl ether, tetrahydrofuran or dioxan.

During the reaction, carried out at a temperature which can range from $-20°$ to $+35°$ C. and preferably at or about 25° C., a precipitate of $MgX_2$ or $MgX_2$ (dioxan) forms rapidly, which is eliminated, and also a second product which remains in solution in the ether. The ethereal solution is recovered and after elimination of the ether a product of formula (2) is obtained, which constitutes the catalyst according to the invention.

In general, one molecule of the ether which has served as the solvent remains combined in the complex; this can be represented by the formula 3:

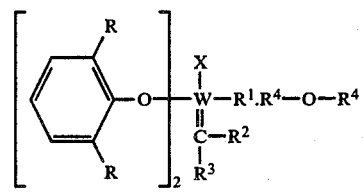

where $R^4$ is a $C_2$ to $C_6$ normal or branched alkyl and preferably $C_2$ or $C_3$, $R^4$—O—$R^4$ can otherwise take a cyclic form particularly

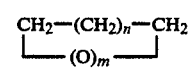

where n is 0 to 4 and n=1 or 2.

The ether molecule attached to the complex is not a co-catalyst but instead a ligand which has formed part of the coordination shell of the tungsten. The nature of this ether ligand can modify the properties of the catalyst, for example the nature of the phenoxy ligands. The formula of the catalyst can generally be written as:

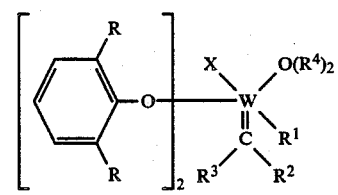

Metathesis, using the new catalyst according to the invention, can be carried out in a manner known per se. While the proportion of the olefin treated per mole of tungsten complex can range widely depending upon the activity of the catalyst, it is usually from 30 to 300 moles per atom of W present and preferably 50 to 150 moles/W.

The temperature, which is also variable with the nature of the reactants present, is generally from 0° to 100° C. and mainly in the range from 50° to 95° C.

The catalysts according to the invention have been tested in the metathesis of several olefins in the absence of any co-catalyst. The following non-limitative examples show the interesting results obtained.

EXAMPLE 1

Preparation of an improved catalyst according to the invention (J)

20 ml of anhydrous diethyl ether, 0.093 g ($1.15 \times 10^{-4}$ mole) of the precursor complex of the formula:

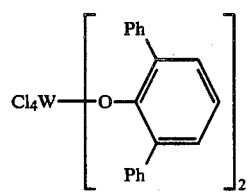

and 0.043 g ($1.7 \times 10^{-4}$ mole) of the organo magnesium compound $Mg(CH_2C(CH_3)_3)_2$ (dioxan), are introduced into a Schlenk tube, previously purged with dry argon. The ethereal solution instantly assumes a brown colour, while a white precipitate of $MgCl_2$ (dioxan) forms. After about 30 minutes of reaction at ambient temperature, the ethereal solution is decanted, filtered and transferred to a second Schlenk tube under argon. After evaporation of the ether, 0.085 g (yield 80%) of a powder having an ochre colour is recovered, the elementary analysis of which conforms to the formula:

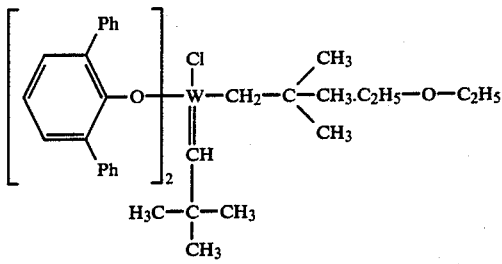

Analysis: calculated: C=64.9%; H=6.2%; Cl=3.8%; W=19.9%; found: C=63.6%; H=5.7%; Cl=3.9%; W=20.1%.

The nuclear magnetic resonance spectrum gives for the H proton of the carbene ligand=$CHC(CH_3)_3$, a resonance signal having a chemical displacement: =9.96 ppm/TMS. The catalyst so synthesized is designated by (J) in the following part of this description. In an analogous manner, catalysts have been synthesized by the reaction of homologous precursors to that of formula (4), in which Ph is replaced by —Cl, —F or —$CH_3$, with the organo-magnesium compound $Mg(CH_2C(CH_3)_3)_2$ dioxan.

EXAMPLES 2 TO 6

Metathesis of an olefin not carrying functional groups (cis-2-pentene)

In these examples, the activities and stereo-selectivities of four catalysts according to the invention, D, E, J and K, are compared with those of the standard catalyst system $WCl_6+Sn(CH_3)_4$.

The catalysts D, E and K correspond to the same formula as J in Example 1, except that:
in D the Ph are replaced by F,
in E the Ph are replaced by $CH_3$,
in K the Ph are replaced by Cl
The tests consist in effecting the metathesis of cis-2-pentene according to the reaction: 2 $CH_3CH=CHCH_2CH_3 \rightleftharpoons CH_3CH=CHCH_3 + CH_3CH_2CH=CHCH_2CH_3$ giving butene-2 and hexene-3.

In a reactor for discontinuous operation, previously purged with argon, there are first introduced $20\times10^{-6}$ moles of the tungsten compound corresponding to D, E, J, K and $100\times10^{-6}$ in the case of $WCl_6+Sn(CH_3)_4$; then 5 ml of chlorobenzene as solvent is poured in. The reactor is heated to 85° C. and cis-2-pentene is introduced into the reactor at the rate of 100 moles per atom of W present. At predetermined time intervals, the gas phase is analysed to determine the proportion and the stereochemistry of the butene-2 formed. Table I (on page 9) indicates the percentages and the cis/trans ratios of the butene-2 formed with variable times for each of the catalysts tested.

It can be confirmed that the catalyst D according to the invention allows the metathesis to attain equilibrium, or 25% conversion, in 20 min, while 55 mins are necessary to arrive at the same point with the standard catalyst of Example 6. On the other hand, it is possible to choose among the catalysts according to the invention those which avoid isomerization of the cis olefin into the trans or in contrast those which favour this transformation. Thus, by using catalyst J (Example 4) and arresting the metathesis at a conversion rate of 14.4%, isomerization is obtained which only gives 0.2 of the trans form for one of the cis, while there is a 1 for 1 ratio with the standard catalyst (Example 6). Also, the trans/cis ratio can be limited to about 0.25 by using the catalyst E (Example 3).

Reciprocally, if it is desirable to increase considerably the trans isomer, a trans/cis ratio of 2.4 can be obtained with the catalyst D in 20 minutes or with K in 55 minutes, the conversion being 25% in the two cases; by contrast, for this it is necessary to operate for about 200 minutes with the standard catalyst (Example 6).

EXAMPLES 7 TO 9

These examples relate to the metathesis of cis-2-pentene effected under the same conditions as in Examples 2 to 6, with homologous catalysts to those designated above by D, J and K but prepared according to Example 1 in diisopropyl ether in place of diethyl ether. The formulae of the complexes employed are thus analogous to that of compound J (see Example 1), the mole of the ether $C_2H_5$—O—$C_2H_5$ being replaced by

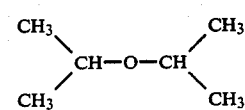

TABLE I

| | Mol. % yields in butene-2 trans/cis ratios (t/c) of butene-2, for the 5 catalysts: | | | | | | | | |
|---|---|---|---|---|---|---|---|---|---|
| Example N° | 2 | | 3 | | 4 | | 5 | | 6 |
| Catalyst | "D" | | "E" | | "J" | | "K" | | $WCl_6 + SnMe_4$ |
| R in formula 2 | fluorine | | methyl | | phenyl | | chlorine | | |
| After a period, in minutes of: | % | t/c | % | t/c | % | t/c | % | t/c | % | t/c |
| 1 | 4 | 0.9 | — | — | — | — | 3.6 | 0.92 | 0.5 | 0.65 |
| 3 | 15 | 1.1 | 1.5 | 0.19 | 0.8 | 0.2 | 9.9 | 1.07 | 2.5 | 0.70 |
| 6 | 20 | 1.5 | 3 | 0.20 | — | — | 17.5 | 1.42 | 6.6 | 0.75 |
| 10 | 24 | 2.2 | 6 | 0.21 | 14.4 | 0.2 | — | — | 14.6 | 1.00 |
| 20 | 25 | 2.4 | 10 | 0.22 | 21 | 0.39 | 22 | 2.32 | 17 | 1.1 |
| 55 | — | — | 14 | 0.25 | 25 | 0.92 | 25 | 2.35 | 25 | 2.0 |
| 200 | — | — | 17 | 0.30 | 25 | 2.5 | 25 | 2.60 | 25 | 2.5 |

In other words, $R^3$ in the formula 3 is an isopropyl. In these complexes, R is formulae 2 and 3 are:
- phenyls for catalyst F,
- Cl atoms for catalyst G and
- F atoms for catalyst H.

It follows that the only difference between these catalysts and those of the preceding examples is their combination with 1 mole of $(CH_3)_2CH-O-CH(CH_3)_2$ in place of $C_2H_5O-C_2H_5$. Thus:

"F" is the analogue of "J" (R=phenyl)
"G" is the analogue of "K" (R=chlorine)
"H" is the analogue of "D" (R=fluorene)

Table II summarises the metathesis results obtained.

TABLE II

Mol. % yields in butene-2 and trans/cis ratios (t/c) of butene-2

| Example n° | 7 | | 8 | | 9 | |
|---|---|---|---|---|---|---|
| Catalyst | F | | G | | H | |
| R in formula 2 | Phenyl | | Chlorine | | Fluorine | |
| After a period, in minutes, of: | % | t/c | % | t/c | % | t/c |
| 1 | 12 | 0.4 | 1 | 0.8 | 0.5 | 0.8 |
| 3 | 22 | 1.0 | 3 | 0.8 | 1.5 | — |
| 6 | 25 | 1.7 | 6.5 | 0.82 | 3.0 | — |
| 10 | 25 | 1.9 | 12 | 0.95 | 4.5 | — |
| 20 | — | — | 21 | 1.4 | 6.0 | 0.8 |
| 55 | — | — | 25 | 2.2 | 7.0 | — |
| 200 | — | — | 25 | 2.5 | 9.0 | 0.9 |

The catalyst F (Example 7) is remarkable in that it allows equilibrium of the metathesis to be reached in 6 minutes; it also slightly advances the trans/cis ratio to about 20% conversion which it reaches in less than 3 minutes.

The catalyst G can be of interest from the standpoint of stereo-chemistry, because it can somewhat vary the amount of the trans isomer to about 12% of conversion (10 minutes). The variation of the t/c ratio is equally slow with catalyst H: between the first and the 200 minute t/c only changes from 0.8 to 0.9.

The comparison between the respective Examples 7 and 4 (F and J), 8 and 5 (G and K) or 9 and 2 (H and D) indicates that the change of the ether $R^3-O-R^3$ in the complex has modified the behaviour of the catalyst in the sence of enlarging the possibilities offered by the invention.

EXAMPLES 10 TO 15

Metathesis of trans-2-pentene

In these examples, the activities and stereo-selectivities of catalysts J, K, D, E, and G, described above are compared with those of the standard catalyst system for metathesis, $W(CO)_5PPh_3.ETAlCl_2+O_2$, use of which is described for example in the publication: M LECONTE and J M BASSET, "Journal of American Chemical Society", 101 (1979) p.7296–7302.

The tests consist in effecting the metathesis of trans-2-pentene according to the reaction $$2CH_3CH=CHCH_2CH_3 \rightleftharpoons CH_3CH=CHCH_3 + CH_3CH_2CH=CHCH_2CH_3$$

giving butene-2 and hexene-3.

The operative conditions are the same as in Examples 2 to 6, except that the quantity of each of the catalysts K, D, E and G, is $20 \times 10^{-6}$ mole, that of J $38 \times 10^{-6}$ mole and that of the catalyst of the prior art $100 \times 10^{-6}$ mole.

Table III indicates the results obtained.

TABLE III

| | Mol. % yields in butene-2 and trans/cis ratios (t/c) of butene-2 | | | | | | | | | | | |
|---|---|---|---|---|---|---|---|---|---|---|---|---|
| Example n° | 10 | | 11 | | 12 | | 13 | | 14 | | 15 | |
| Catalyst | D | | E | | G* | | J | | K | | $W(CO)_5PPh_3$ + 4 $EtAlCl_2$ + 0.5 $O_2$ | |
| R in formula 2 | Fluorine | | Methyl | | Chlorine | | Phenyl | | Chlorine | | | |
| after a period, in minutes, of: | % | t/c | % | t/c | % | t/c | % | t/c | % | t/c | % | t/c |
| 0.5 | 1 | 5.3 | — | — | — | — | 2 | 9.5 | 2 | 7.2 | 0.5 | 1.25 |
| 2 | 4 | 5.3 | — | — | 1.5 | 8.1 | 12 | 9.5 | 10 | 2.6 | 8 | 1.61 |
| 5 | 10 | 4.3 | 1.5 | 9.6 | 9 | 5.7 | 19 | 9.5 | 25 | 2.4 | 12 | 1.72 |
| 15 | 24 | 2.4 | 3.4 | 9.1 | 24 | 2.4 | 22 | 3.8 | 25 | 2.4 | 16.5 | 1.91 |
| 30 | 25 | 2.4 | 6.0 | 8.5 | 25 | 2.4 | 25 | 3.0 | — | — | 19.5 | 1.95 |
| 60 | — | — | 10 | 7.4 | — | — | 25 | 2.6 | — | — | 22 | 2.00 |
| 180 | — | — | 18 | 5.5 | — | — | — | — | — | — | 25 | 2.40 |

*Complex with $(CH_3)_2CH-O-CH(CH_3)_2$ in place of $C_2H_5-O-C_2H_5$ in the other catalysts.

It can be seen that the catalysts D, G, J and K are remarkable from the standpoint of activity, since they permit obtaining equilibrium at 25% conversion in 15 to 30 minutes, while 180 minutes are necessary with the prior art catalyst (Example 15).

On the other hand, all the catalysts (D to K) according to the invention are of considerable interest for obtaining butene-2 rich in the trans form, that is with an elevated t/c ratio. It is sufficient in certain cases to use a more limited conversion, to obtain a butene having 90% of the trans isomer. In contrast, the known catalyst $W(CO)_5PPh_3$, always gives a product containing more than 29% of the cis form.

These facts are illustrated below in Table IV by information obtained from Table III. The trans isomer contents are calculated for different yields of butene expressed in mol.%.

TABLE IV

| Example n° | Catalyst | Time in mn | Yield mol % | % trans |
|---|---|---|---|---|
| 10 | D | 5' | 10 | 81 |
| 11 | E | 60' | 10 | 88 |
| " | " | 180' | 18 | 84 |
| 12 | G | 5' | 9 | 85 |
| " | " | 15' | 24 | 70 |
| 13 | J | 5' | 19 | 90 |
| " | " | 15' | 22 | 79 |
| 14 | K | 2' | 10 | 72 |
| " | " | 5' | 25 | 70 |
| 15 | $W(CO)_5PPh_3$ | 5' | 12 | 63 |
| " | " | 60" | 22 | 67 |
| " | " | 180' | 25 | 70 |

Thus, with the catalysts according to the invention, the trans isomer content of 70 to 90% can be obtained on average for a duration of metathesis of about 5 to 60 minutes, while the prior art catalyst (Example 15) only gives 60 to 70%, and, to obtain 70%, 180 minutes are necessary.

It is also of interest to note in addition that the particular properties of the catalyst according to the invention can be influenced by the nature of the ether combined with the complex. It can be seen in effect that K, carrying a mole of $C_2H_5OC_2H_5$, is of greater interest for the kinetics of the metathesis, but much less as regards the stereo-selectivity than G which contains an isopropyl ether mole $[(CH_3)_2CH]_2O$.

EXAMPLES 16 TO 18

Metathesis of an olefin carrying functional groups (cis ethyl oleate)

The tests consist in maintaining cis-ethyl oleate at 80° C., in the presence of a catalyst having a W base, and determining the percentage of octadecene-9 and the stereo-chemistry of this octadecene formed according the equilibrium reaction:

$$CH_3(CH_2)_7CH$$
$$\|$$
$$C_2H_5OOC(CH_2)_7CH \;+$$

$$\underset{\|}{CH(CH_2)_7CH_3} \qquad \underset{\|}{CH_3(CH_2)_7CH}$$
$$CH(CH_2)_7COOC_2H_5 \rightleftarrows CH_3(CH_2)_7CH \;+$$

$$C_2H_5OOC(CH_2)_7CH\!=\!CH(CH_2)_7COOC_2H_5$$

which provides at the same time hexadecene-8-di-1,16-ethyl carboxylate.

The reaction is carried out in an apparatus for discontinuous operation previously purged with argon in which is introduced $10^{-4}$ mole of the tungsten compound, if required with a co-catalyst in a quantity which is indicated in Table V, and 5 ml of chlorobenzene as solvent. After heating the reactor to 80° C., the cis-ethyl oleate is introduced in the quantity indicated in Table V in the form of a number of moles of the oleate per atom of W present.

At predetermined time intervals, the liquid phase in the reactor is analysed, to determine the yield of octadecene-9, that is the percentage ratio of the number of moles of this compound formed to the number of moles of the oleate used; the trans-octadecene-9/cisoctadecene-9 ratio is also determined. The catalyst system designated by "WPb" (Example 17) is constituted by

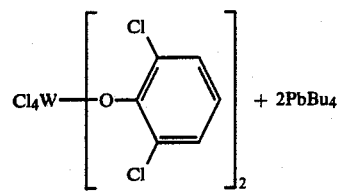

which is mentioned in French Pat. No. 8409001.

TABLE V

| | Mol/% yields in octadecene-9 trans/cis octadecene-9 ratios (t/c) | | |
|---|---|---|---|
| Example n° | 16 | 17 | 18 |
| Catalyst | J | "WPb" | $WCl_6 + 2SnMe_4$ |
| Ethyl oleate mol W mol | 125 | 50 | 50 |
| After times in min: | % t/c | % t/c | % |
| 10 | 13.5  0.55 | 5  1.8 | — |
| 30 | 16  1.0 | 14  2.57 | 4.2 |
| 60 | 16  1.42 | 14  2.70 | — |
| 120 | —  — | 14  — | 5.0 |
| 1200 | 16  4.0 | 15  4.20 | 6.0 |

These results show that the catalyst J of the invention is much more active without any co-catalyst than the standard catalyst system (Example 18) $WCl_6 + SnMe_4$; it is also more active than the catalyst system of Patent Application 8409001 (Example 17). In effect, even with a much higher oleate/W ratio, with catalyst J a yield of 13.5% of octadecene-9 is obtained after 10 minutes, while after the same time this yield is only 5% with the catalyst system of example 17.

The catalyst J according to the invention is also particularly of interest for its stereo-selectivity. In effect, at a yield of 13.5% approaching the maximum yield which is 16%, it is observed that the octadecene-9 formed is still cis to in the major part (64.5% cis), while the thermodynamic equilibrium is clearly in favour of the trans product. In contrast, with the catalyst of Example 17 at only 5% yield, the trans/cis ratio is already equal to 1.8, that is the proportion of cis is no more than 35.7%.

EXAMPLES 19 TO 22

Use of catalysts according to the invention for the cross metathesis of olefinic acid esters and olefins with a view to the synthesis of insect pheromones The reaction studied is:

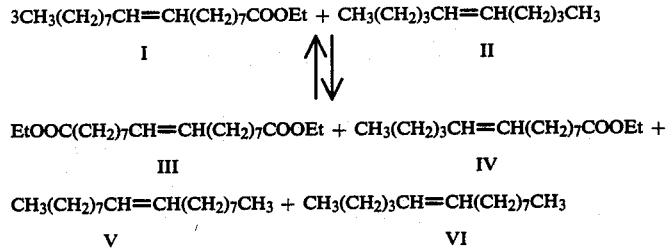

This reaction between ethyl oleate and decene-5 has been carried out in an apparatus of the discontinuous type suitably purged with argon. The reactants were introduced in the following order:

$0.33 \times 10^{-4}$ mole of catalyst, 5 ml of chlorobenzene (solvent), 0.125×10⁻² mole of ethyl oleate +0.25×10⁻² mole decene-5.

The reactor is heated to 85° C. and analysis of the liquid phase during this time allows the conversion to be determined in mole percent of initial oleate and the selectivity (mole %) of product IV; this selectivity represents the quantity of the product IV formed in relation to the quantity of ethyl oleate converted.

Table VI summarises the results obtained with the catalysts F and J according to the invention, in comparison with the prior art using the catalyst systems:

(WCl₆+SnMe₄) designated by "WSn" and

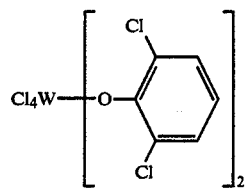

+PbBu₄ designated by "WPb"

TABLE VI

| EXAMPLES n° | Catalyst | Molar ratio (I + II)/W | Reaction Time | Conversion of I | Selectivity in IV |
|---|---|---|---|---|---|
| 19 | "WSn" | 50 | 1 h | 50% | 35% |
|  |  |  | 5 h | 60% | 40% |
| 20 | "WPb" | 112 | 1 h | 72% | 66% |
|  |  |  | 2 h | 72% | 66% |
| 21 | J | 112 | ½ h | 60% | 90% |
|  |  |  | 2 h 30 | 80% | 90% |
|  |  |  | 4 h 30 | 84% | 90% |
| 22 | F | 150 | ¼ h | 66% | 88% |
|  |  |  | ½ h | 80% | 88% |
|  |  |  | 1 h | 86% | 88% |

It can be seen that in the absence of any cocatalyst, the complexes F and J according to the invention allow the crossed metathesis reaction between ethyl oleate and decene-5 to be carried out with much higher speeds and much better selectivities than the prior art catalyst systems, even when they have been improved ("WPb"-Example 20). In effect, if the conversion curve is plotted as a function of time starting from the data given in Table VI, the following losses in % per hour, during the first hour, are found:

| n° |  |  |
|---|---|---|
| 19 | "WSn" | 50 |
| 20 | "WPb" | 72 |
| 21 | J | 100 |
| 22 | F | 145 |

Also, with the known catalysts, a 72% conversion is not exceeded, while this attains 86% with the catalysts of the invention. As regards selectivities, they are from 88 to 90% as against 40 to 60% for the prior art.

EXAMPLE 23

Polymerisation by the metathesis of a cyclic olefin

Polymerisation by the metathesis of dicyclopentadiene is effected with the aid of catalysts (K), (D), (F) and (G) of the invention, each used in a discontinuous operation.

In an apparatus purged with argon, the following quantities of reactants are introduced in the order:

0.5×10⁻⁴ mole of catalyst (K), (D), (F) or (G)

5 ml of chlorobenzene as solvent, 3.4 ml or 2.5×10⁻² mole of dicyclopentadiene.

The reaction is carried out at 25° C. for 10 minutes. A yield of 100% of the polymer is found, in each of the four tests.

The polymers obtained by the process of the invention can be used for any known means and in particular for pull extrusion.

We claim:

1. Improved process for the metathesis of olefins comprising contact of at least one olefin with a catalyst characterised in that the catalyst is of the formula

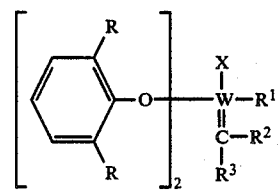

where X is a halogen, R is a hydrocarbon group or an electronegative group or atom, R¹ is an alkyl group, and R² and R³ individually are hydrogen atoms or straight or branched C₁ to C₈ alkyl groups.

2. Process according to claim 1, characterized in that at least one molecule of an ether R⁴—O—R⁴ is complexed in the catalyst, R⁴ being a C₂ to C₆ alkyl.

3. Process according to claim 2 wherein R⁴ is ethyl or isopropyl.

4. Process according to claim 1, characterised in that at least one molecule of dioxane or an ether

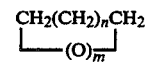

is complexed in the catalyst, where n is an integer of 0 to 6 and m=1.

5. Process according to claim 1, characterised in that the catalyst is employed without any co-catalyst between 0° and 100° C. and the proportion of olefin is from 30 to 300 moles per atom of W present.

6. Process according to claim 5 wherein said temperature is 50°-95° C. and the proportion of olefin is 50-150 moles per atom of W present.

7. Process according to claim 1 characterised in that the catalyst is employed with a Lewis acid co-catalyst.

8. Process according to claim 7 characterized in that said co-catalyst is an organo aluminum, tin, lead, magnesium or titanium compound Lewis acid.

9. Process according to claim 1 wherein R¹ is a C₁₋₈ alkyl group.

10. Process according to claim 1 characterized in that R is phenyl, methyl, Cl or F, R¹ is neopentyl, R² is tert-butyl, R³ is hydrogen and said catalyst contains complexed therein at least one molecule of diethyl ether or diisopropyl ether.

11. Catalyst for carrying out the metathesis comprising a diphenoxy tungsten complex, characterised by the structure

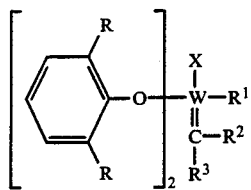

(1)

where X is a halogen, R is a hydrocarbon group or an electro-negative group or atom, $R^1$ is an alkyl group, and $R^2$ and $R^3$ individually are hydrogen atoms or straight or branched $C_1$ to $C_8$ alkyl groups.

12. Catalyst according to claim 11, characterised in that a mole of ether $R^4OR^4$ or

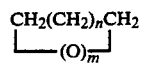

is combined with the molecule of the complex, $R^4$ being a $C_2$ to $C_6$ alkyl, n being 0 to 6 and m=1 or 2.

13. Catalyst according to claim 11, characterised in that R is phenyl, methyl, Cl or F $R^1$ is a neopentyl, $R^2$ is a tert-butyl and $R^3$ is a hydrogen atom.

14. Catalyst according to claim 12, characterised in that $R^4$ is ethyl or an isopropyl.

15. Process of preparation of a complex catalyst according to claim 11, characterised in that Mg(CHR'R")$_2$ wherein R' and R" are H or alkyl is reacted with a tetra-halogeno complex of di-phenoxy tungsten

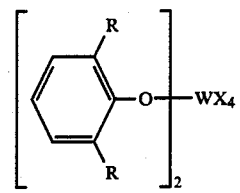

in an ether.

16. Catalyst according to claim 11 wherein $R^1$ is $C_{1-8}$ alkyl.

17. Catalyst according to claim 13 characterized in that a mole of diethyl ether or diisopropyl ether is combined with the molecule of the diphenoxy tungsten complex.

* * * * *